US012746138B2

(12) United States Patent
Sondrup

(10) Patent No.: US 12,746,138 B2
(45) Date of Patent: Sep. 29, 2026

(54) KNEE CUSHION APPARATUS

(71) Applicant: Sleep Gear LLC, Henderson, NV (US)

(72) Inventor: Stuart Sondrup, Farmington, UT (US)

( * ) Notice: Subject to any disclaimer, the term of this patent is extended or adjusted under 35 U.S.C. 154(b) by 148 days.

(21) Appl. No.: 18/161,877

(22) Filed: Jan. 30, 2023

(65) Prior Publication Data

US 2023/0240875 A1 Aug. 3, 2023

Related U.S. Application Data

(60) Provisional application No. 63/304,596, filed on Jan. 29, 2022.

(51) Int. Cl.

| | |
|---|---|
| ***A61F 5/01*** | (2006.01) |
| ***A47G 9/10*** | (2006.01) |
| ***A61F 13/06*** | (2006.01) |
| *A47C 20/02* | (2006.01) |

(52) U.S. Cl.

CPC .............. *A61F 5/0109* (2013.01); *A47G 9/10* (2013.01); *A61F 13/061* (2013.01); *A47C 20/021* (2013.01)

(58) Field of Classification Search

CPC ........ A61F 5/0109; A61F 5/30; A61F 13/061; A61G 7/075; A61G 7/0755; A47C 20/021; A47G 9/10

See application file for complete search history.

(56) References Cited

U.S. PATENT DOCUMENTS 4,177,806 A * 12/1979 Griffin .................. A61F 13/062 128/892
4,250,578 A * 2/1981 Barlow ................ A41D 13/065 2/24
4,706,302 A * 11/1987 Padfield ............ A41D 13/0568 2/24
4,736,477 A * 4/1988 Moore ................. A47C 20/021 128/892
4,905,715 A * 3/1990 Johnson .................. A61F 13/06 128/882
5,377,693 A * 1/1995 Loper ....................... A61F 5/00 128/845
5,418,991 A * 5/1995 Shiflett ..................... A61F 5/01 5/648
5,465,736 A * 11/1995 Lonardo ................. A61F 13/06 128/892
5,953,777 A * 9/1999 Buck .................... A47G 9/0253 5/636
6,145,508 A * 11/2000 Seip, Jr. ............... A47C 20/021 128/845

(Continued)

*Primary Examiner* — Keri J Nelson

(57) ABSTRACT

An apparatus includes a sleeve configured to be worn on a knee of a user and a compartment coupled to the sleeve. The includes an upper opening and lower opening. The compartment is configured to be located on an inside of the knee when the sleeve is worn such that the compartment is positioned between the knees of the user. The upper opening is positioned above the knee of the user and the lower opening is positioned below the knee of the user. The apparatus further includes a compressible padding enclosed within the compartment such that the compressible padding is configured to positioned between a user's knees when they sleep on their side. The compressible padding separates the legs of the user to align the legs and back of the user when they sleep on their side.

13 Claims, 4 Drawing Sheets

(56) References Cited

U.S. PATENT DOCUMENTS

| | | | | |
|---|---|---|---|---|
| 6,182,311 | B1 * | 2/2001 | Buchanan | A47C 20/021<br>128/845 |
| 6,760,936 | B1 * | 7/2004 | Lloyd | A47C 20/025<br>2/24 |
| 6,807,697 | B2 * | 10/2004 | Druery | A61F 5/01<br>5/640 |
| 7,536,735 | B1 * | 5/2009 | Stump | A47G 9/10<br>5/636 |
| 9,603,458 | B2 * | 3/2017 | Pelletier | A47C 20/021 |
| 9,648,959 | B2 * | 5/2017 | Frydman | A47C 20/021 |
| 2012/0041488 | A1 * | 2/2012 | Al Mubayadh | A61F 5/01<br>606/237 |
| 2013/0074269 | A1 * | 3/2013 | Phillips, II | A61F 5/0193<br>5/648 |
| 2020/0107644 | A1 * | 4/2020 | Dubois | A47C 27/088 |
| 2022/0408934 | A1 * | 12/2022 | Mansour | A47C 20/021 |
| 2024/0341509 | A1 * | 10/2024 | Rubin | A41D 20/00 |

* cited by examiner

KNEE CUSHION APPARATUS

CROSS REFERENCE TO RELATED APPLICATION

This application claims the benefit of U.S. Provisional Application No. 63/304,596, filed on Jan. 29, 2020, which is incorporated by reference herein in its entirety.

FIELD

This invention relates to a sleep apparatus and more particularly relates to an apparatus that aligns the legs and back of a side sleeper.

BACKGROUND

It is important for individuals to sleep properly, not only to maintain and improve their physical well-being but to avoid over-stressing or injuring specific muscles, joints, or other parts of the body during sleep. Persons who sleep on their side tend to have misalignments between their legs and back. One way such people have somewhat helped such situations is to sleep with a pillow between their legs. Unfortunately, this becomes problematic once the sleeper wished to change positions or even moves slightly. The pillow can fall out leaving little protection and help to the person. In addition, having to fumble with a pillow while one tries to sleep can interrupt sleep patterns and result in a less deep sleep. Embodiments described herein allow for a better more restful sleep. Embodiments herein allow for consistent alignment of legs and back such to help ensure that a user wakes up refreshed and rested and not stiff and sore.

Embodiments of the present invention allow for the optimization of alignment of a person's legs with a consistent distance between the knees. Other aspects and advantages of embodiments of the present invention will become apparent from the following detailed description, taken in conjunction with the accompanying drawings, illustrated by way of example of the principles of the invention.

SUMMARY

The subject matter of the present application has been developed in response to the present state of the art, and in particular, in response to the problems and disadvantages associated with conventional systems that have not yet been fully solved by currently available techniques. Accordingly, the subject matter of the present application has been developed to provide embodiments that overcome at least some of the shortcomings of prior art techniques.

Embodiments of an apparatus are described. An apparatus includes a sleeve configured to be worn on a knee of a user and a compartment coupled to the sleeve. The includes an upper opening and lower opening. The compartment is configured to be located on an inside of the knee when the sleeve is worn such that the compartment is positioned between the knees of the user. The upper opening is positioned above the knee of the user and the lower opening is positioned below the knee of the user. The apparatus further includes a compressible padding enclosed within the compartment such that the compressible padding is configured to positioned between a user's knees when they sleep on their side. The compressible padding separates the legs of the user to align the legs and back of the user when they sleep on their side. The preceding subject matter of this paragraph characterizes example 1 of the present disclosure.

The sleeve is a tube of material configured to compress on the knee of the user such that the compartment will stay in position relative to the knee and the compressible padding will stay between the knees of the user. The preceding subject matter of this paragraph characterizes example 2 of the present disclosure, wherein example 2 also includes the subject matter according to example 1, above.

The sleeve is symmetrical from front to back such that either knee of the user may be inserted into the sleeve with the compartment on the inside of the knee. The preceding subject matter of this paragraph characterizes example 3 of the present disclosure, wherein example 3 also includes the subject matter according to any one of examples 1-2, above.

The sleeve includes a hole, wherein the kneecap is configured to sit in the hole. The preceding subject matter of this paragraph characterizes example 4 of the present disclosure, wherein example 4 also includes the subject matter according to any one of examples 1-3, above.

The sleeve is made of a flexible and a stretchable fabric. The preceding subject matter of this paragraph characterizes example 5 of the present disclosure, wherein example 5 also includes the subject matter according to any one of examples 1-4, above.

The compartment is coupled to the sleeve by a stitching, and wherein the stitching runs circumferentially around a back side of the compartment. The preceding subject matter of this paragraph characterizes example 6 of the present disclosure, wherein example 6 also includes the subject matter according to any one of examples 1-5, above.

The compartment is coupled to the sleeve by a stitching, and wherein the stitching only runs on a single edge of a back side of the compartment such that the compartment may be flipped along the single edge into and out of position. The preceding subject matter of this paragraph characterizes example 7 of the present disclosure, wherein example 7 also includes the subject matter according to any one of examples 1-6, above.

compartment is coupled to the sleeve by a hook and loop fastener. The preceding subject matter of this paragraph characterizes example 8 of the present disclosure, wherein example 8 also includes the subject matter according to any one of examples 1-7, above.

The compartment is coupled to the sleeve by straps that extend through the sleeve. The preceding subject matter of this paragraph characterizes example 9 of the present disclosure, wherein example 9 also includes the subject matter according to any one of examples 1-8, above.

The sleeve is configured to be worn on either knee. The preceding subject matter of this paragraph characterizes example 10 of the present disclosure, wherein example 10 also includes the subject matter according to any one of examples 1-9, above.

The padding includes separate cushion pads, wherein the number of cushion pads can be adjusted by the user to change an overall thickness of the padding between the knees. The preceding subject matter of this paragraph characterizes example 11 of the present disclosure, wherein example 11 also includes the subject matter according to any one of examples 1-10, above.

The compartment includes an opening where the padding is inserted into or removed from the compartment. The preceding subject matter of this paragraph characterizes example 12 of the present disclosure, wherein example 12 also includes the subject matter according to any one of examples 1-11, above.

The compartment includes an opening where the padding is inserted into or removed from the compartment, wherein the padding includes more than one cushion pads of differing thicknesses. The preceding subject matter of this paragraph characterizes example 13 of the present disclosure, wherein example 13 also includes the subject matter according to any one of examples 1-12, above.

The upper opening and the lower opening are the same size. The preceding subject matter of this paragraph characterizes example 14 of the present disclosure, wherein example 14 also includes the subject matter according to any one of examples 1-13, above.

The upper opening is larger in size than the lower opening. The preceding subject matter of this paragraph characterizes example 15 of the present disclosure, wherein example 15 also includes the subject matter according to any one of examples 1-14, above.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

Throughout the description, similar reference numbers may be used to identify similar elements.

DETAILED DESCRIPTION

Figure 1:
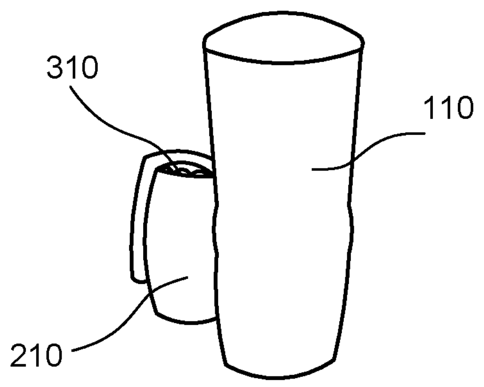
FIG. 1 depicts a front view of a knee cushion apparatus according to one or more embodiments of the present disclosure.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

FIG. 1 depicts a front view of a knee cushion apparatus according to one or more embodiments of the present disclosure. The apparatus includes a sleeve 110. The sleeve 110 is configured to be worn on the knee of a user. The sleeve 110 may be made of a stretchable material and be sized to fit snugly on the knee of a user. Such a tight fit allows for a user to securely position the apparatus on the knee and position the padding in the appropriate area such that the padding does not move out of position while the user is asleep or when the user moves around in their bed.

In the illustrated embodiment, the apparatus is coupled to the knee of a user by a fabric sleeve. Other attachment mechanisms are envisioned. In some embodiments, the sleeve is embodied as straps to couple to the apparatus to the knee. In such an implementation, an attachment strap may be employed above the knee and another attachment strap below the knee. The attachment straps may securely position the apparatus on the knee allowing the user to move around without disturbing the general positioning of the padding.

In another embodiment, the sleeve is a knee brace. A knee injury may lead to someone using a knee brace during recovery for stability and other reasons. The apparatus may employ a knee brace as the mechanism for coupling the apparatus to the user.

In other embodiments, the apparatus may include a sock (or more particularly a compression sock) that extends up the leg and above the knee. The sock may securely position the apparatus on the knee and the padding in the inside of the knee. Other mechanisms for attaching or coupling the apparatus to the knee are described and envisioned throughout the description.

The illustrated embodiment includes a compartment 210. The compartment 210 may be shaped and sized differently depending on the size of the wearer. In some embodiments, the compartment 210 extends two inches below the knee and two inches above the knee. In some embodiments, the compartment 210 extends one inch below and above the knee. In some embodiments, the compartment 210 just covers the inside of the knee.

In the illustrated embodiment, the compartment 210 includes an opening on the upper part of the compartment 210. The opening allows for objects to be place within and housed within the compartment 210. In the illustrated embodiment there are three sections of foam pad housed within the compartment. The three sections of foam pad are removable from the compartment 210. This allows a user to modify the thickness of the padding. The overall thickness of the padding will dictate the distance between the knees of a user when they are sleeping on their side and allow for proper alignment of the back and legs of the user. The padding level can be adjusted or, in other words, is adjustable. With an open compartment, the padding thickness is easily adjustable for a user so that they can reach maximal efficiency in alignment. Such thickness can be dictated with the help of a medical professional or practitioner.

In the illustrated embodiment, the compartment 210 is flexible and stretchable allowing for the adjustment of the padding level. The compartment 210 will allow the user to insert more foam pads than are shown. As an example, the compartment may include a single pad. In other embodiments, the compartment may include two pads. In other embodiments, the compartment may include three pads. The flexibility is possible in such embodiments because the compartment 210 includes an opening.

In the illustrated, the opening is located on a single side of the compartment. As a convention, the back side of the compartment is fastened or sewn to the sleeve 110. This may be done by stitching or other means such as Velcro or other known means. In the illustrated embodiment, the compartment 210 is sewn with stitching running the circumference of the back side of the compartment 210. In some embodiments, the compartment is a completely enclosable pouch with fabric on the backside of the compartment 210. In other embodiments, the sleeve 110 forms the backside of the compartment 210 as the compartment is sewn onto the sleeve 110. In such embodiments, there is no fabric or material between the padding and the sleeve 110, such that the padding is contacting the sleeve 110 on the backside of the compartment 210.

In some embodiments, the compartment 210 is fastened to the sleeve 110 on two opposite edges of the back side of the compartment 210. This allows for the additional padding to be placed not only within the compartment 210 but also between the compartment and sleeve 110. In such embodiments, the compartment 210 includes fabric or material on the back side of the compartment 210.

In some embodiments, the compartment 210 is coupled to the sleeve 110 on only a single edge of the back side of the compartment 210. Such embodiments would allow for the user to flip the compartment 210 and padding into and out of position depending on the user's preference. This would allow a user to functionally move the compartment out of the way during a portion of sleep if desired. In some embodiments, the edge that is coupled to the sleeve 110 may be located on the front side, such that the edge is near the knee cap of the user. This would allow the user to flip the compartment to a position in front of the kneecap.

In another embodiment, the compartment 210 is coupled to the sleeve 110 on rear side, such that the edge is near the knee pit of the user. This would allow the user to flip the compartment to a position behind the knee. This may be advantageous for a user that sometimes sleeps on their back and would like support or cushioning behind the knee. This could be beneficial for user's that would like their knee slightly bend when lying on their back. In such a configuration, a user could wear two apparatuses, one on each knee.

In many embodiments, the opening in the compartment is on a single side of the compartment 210. In the illustrated embodiment, the opening is on the top of the compartment 210. By convention herein, this is located above the user's knee (between their thighs). This can be beneficial as the user is up walking around because the opening will be on the top and the padding will be secure. In other embodiments, the opening may be located on the bottom of the compartment such that it is below the knees. This is not ideal but may be more convenient in scenarios where the apparatus is used by someone who is bedridden and does not change the padding themselves. The opening will be accessible for an assistant with the opening on the bottom and won't require the assistant to insert the padding between the user's thighs to add or remove padding. As also contemplated herein, the opening may be located on the front side on the side near the knee cap. This may also create an ease of access if needed.

In nearly all embodiments, the compartment 210 is flexible such that the compartment 210 may change shape to conform to a user's knees. In many embodiments, the compartment 210 is stretchable also, such that the volume of the compartment may expand when more padding is inserted into the compartment 210.

In some embodiments, the opening is left exposed with no covering. In many embodiments, the opening is covered by some means or fabric. For example, in the illustrated embodiment, the compartment 210 includes a flap. The flap is attached on the side near the sleeve 110 and folds over the opening of the compartment 210 after the padding is inserted such that the compartment is functionally closed. In some embodiments, the flap may be releasable coupled to the compartment, such that the flap stays in a closed position. This could be accomplished by Velcro, buttons, or the like.

In other embodiments, the flap may be attached to the compartment on the side away from the sleeve 110 and fold towards the sleeve, folding over the opening of the compartment 210. Such embodiments may reduce discomfort of the user because the flap doesn't move around on the inside of the knee when a user moves around.

In other embodiments, the compartment 210 can be closed by other means including, but not limited to, a zipper, buttons, fasteners, clips, and folds. In the illustrated embodiment, the opening is at a top of the compartment. In some embodiments, the opening is in the middle of the compartment on the side away from the sleeve 110. In one implementation, the opening is just overlapping fabric that form a seam between them.

Within the compartment 210, are cushion pads 310. In the illustrated embodiment, there are three cushion pads 310. These may be foam pads or other compressible materials. In some embodiments, the compartment 210 is able to have varying numbers of cushion pads 310, allowing a user to customize the proper amount of cushioning between the knees that suits their body structure and composition. This allows persons of all different sizes to use an amount that allows for correct alignment of body parts while they sleep.

Other compressible material may be housed within the compartment 210 that allows for proper stability and comfort for the knees while one sleeps. In addition, embodiments of the invention allow for a user to toss and turn and sleep in a myriad of positions without disturbing the cushion pads 310. A user can sleep on either side or on their back. If sleeping on their back, once they turn to their side, the apparatus is positioned such that it stays on the interior of the knee and will be positioned between the knees of the user.

In the illustrated embodiment, the cushion pads 310 encompass the entirety of the compartment. Stated another way, the cushion pads 310 extend from the bottom of the compartment to the top and all the way from the front side to the rear side of the compartment 210. This makes it so that the cushion pads 310 don't move around from side to side or up and down within the compartment 210. What is desired is that the cushion pads 310 stay in position between the two knees of the user and that the pads do not unnecessarily move around and out of position within the compartment 210.

Figure 2:
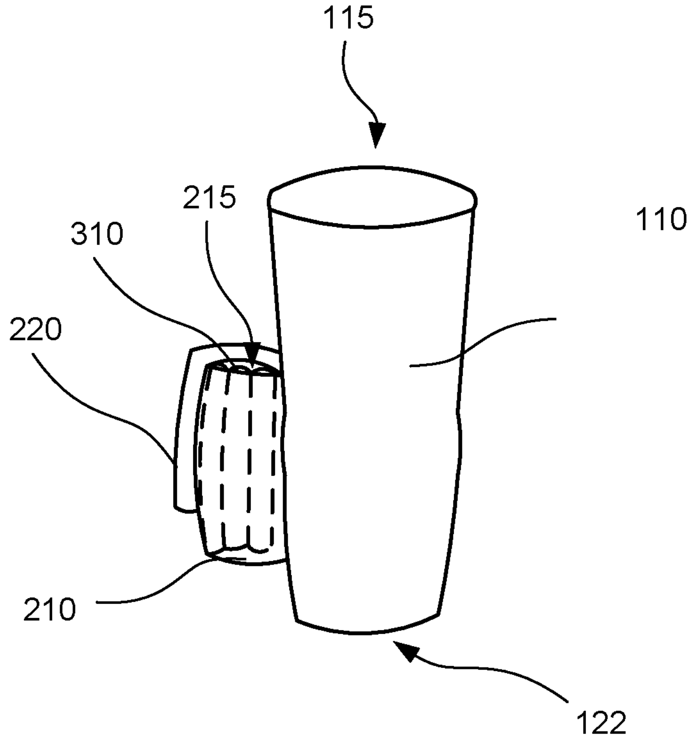
FIG. 2 depicts a front view of a knee cushion apparatus according to one or more embodiments of the present disclosure.

FIG. 2 depicts a front view of a knee cushion apparatus according to one or more embodiments of the present disclosure. In the illustrated embodiment, the cushion pads 310 are shown (with dashed lines) within the compartment 210 of the apparatus. This Figure shows how the cushion pads 310 are situated within the compartment 210. As can be seen, the cushion pads 310 extend from the bottom of the compartment to the top of the compartment. The cushion pads 310 also extend all the way from the front side to the rear side of the compartment 210. This makes it so that the cushion pads 310 don't move around from side to side or up and down within the compartment 210. The three cushion pads 310 are all the same size. That is, they are the same shape and dimensions such that they are interchangeable and can be positioned in whatever order. All three pads 310 may have the same thicknesses. In some embodiments, the cushion pads 310 may have different thicknesses. This would allow a user to better vary the overall thickness of multiple cushion pads such that different permutations of pads results in different overall thicknesses. When the cushion pads 310 are all the same thickness, there would be just periodic, discrete variations in overall thickness of the cushion pads.

As also shown in FIG. 2, the opening 215 of the compartment 210 is shown. In addition, the flap 220 is identified. Also shown is an upper opening 115 of the sleeve 110. This is where the user would insert their foot while pulling up the sleeve 110 onto their knee. There is also a lower opening in the sleeve where the foot would come out while pulling the sleeve 110 onto the knee.

As shown in FIGS. 1 and 2, the sleeve 110 may be configured to go on either knee. As an example, if the sleeve 110 were placed on a user's left knee, then the portion of the sleeve 110 that is visible in the Figures would be covering the user's knee cap such that the compartment 210 and the cushion pads 310 are located on the inside of the left knee and the right knee would contact the compartment 210 when the knees are brought together. The apparatus could be placed on a user's right knee as well. In such an example, the portion of the sleeve 110 this visible in the Figures would be covering the user's knee pit such that the compartment 210 and the cushion pads 310 are located on the inside of the right knee and the left knee would contact the compartment 210 when the knees are brought together.

The use of a flexible and somewhat stretchable material for the sleeve 110 allows for the user to put the apparatus on whichever knee they choose. Obviously, the user would be able to rotate the apparatus from leg to leg on different nights to make sure that the knees could take turns being covered or exposed while the compartment is always between the knees. In this illustrated embodiment, the sleeve is symmetrical from front to back. That is, either side may function as the front where the knee cap will be located.

In the illustrated embodiment, the upper opening 115 of the sleeve 110 may be larger than the lower opening 122. This may be because user's typically have larger thighs than calves. In some embodiments, the upper opening 115 and the lower opening may be identical. This would allow a user to rotate or change how they slide the apparatus on their knee. This may be advantageous because the sleeve 110 is stretchable and a user's thicker thighs may slowly stretch out what is considered the upper opening 115 over time. After that occurs, a user may flip the apparatus upside down such that what was originally considered to be the upper opening 115 is now the lower opening 122 (at least with respect to how the leg is inserted into the sleeve 110. This obviously may result in the opening 215 of the compartment now being located on the bottom and not the top (at least relative to the knee). This just allows for a user to have more flexibility on how they put on the apparatus.

In embodiments where the upper opening 115 and the lower opening 122 are different sizes, this also allows for the user to select the proper opening that they would like to be compressed on their thigh. This may be thought of because there may be user's with a relatively skinny thigh that wish to use the smaller of the two openings on their thigh to make sure the sleeve 110 stays snug on the leg while another user with a relatively thicker thigh may wish to use the larger of the two openings on their thigh to make sure that the sleeve 110 doesn't unnecessarily constrict their thigh. In such functionality, the apparatus is flexible to user's needs and the same size apparatus can be utilized by user's of different physical size.

Figure 3:
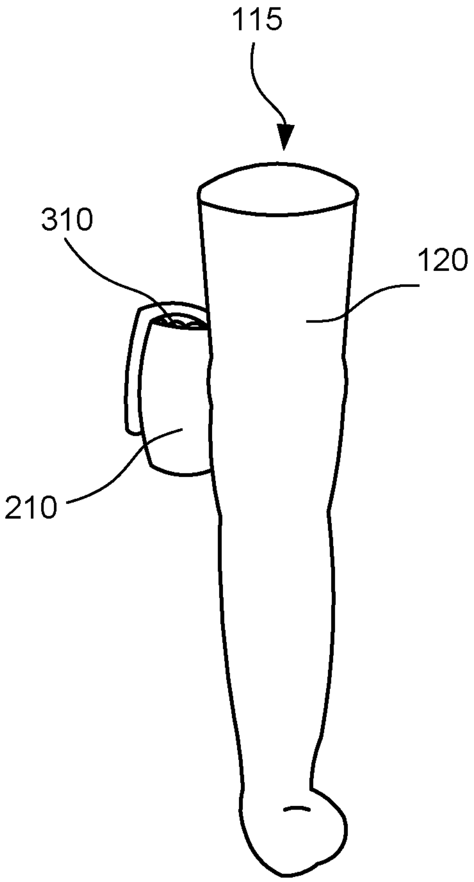
FIG. 3 depicts a front view of a knee cushion apparatus according to one or more embodiments of the present disclosure.

FIG. 3 depicts a front view of a knee cushion apparatus according to one or more embodiments of the present disclosure. In the illustrated embodiment, a compression sock 120 is used. The compression sock 120 is used similar to the way the sleeve 110 is utilized in the embodiments shown in FIGS. 1 and 2. The compression sock 120 will have the compartment 210 (and thus the cushion pads 310) positioned such that the cushions are located on the inside of the user's knee. All the features and different variations discussed above with regard to FIGS. 1 and 2 may also be implemented with the embodiment of FIG. 3 and are only not repeated here for the sake of brevity. Although described as a compression sock, any type of sock (or nylon) may be used. The compression sock 120 only includes a single upper opening 115. This obviously limits the flexibility for the user but the compression sock may still be used on either knee.

Figure 4:
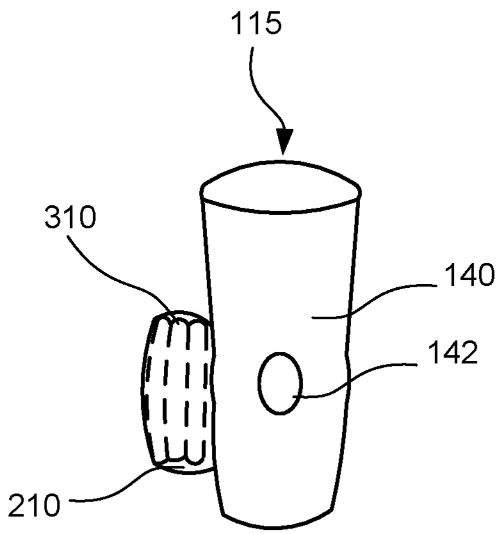
FIG. 4 illustrates a front view of a knee cushion apparatus according to one or more embodiments of the present disclosure.

FIG. 4 illustrates a front view of a knee cushion apparatus according to one or more embodiments of the present disclosure. In the illustrated embodiment, a knee brace 140 is used. The knee brace 140 includes a hole 142 for the kneecap that is present on many knee braces. All types of knee braces are envisioned herein as suitable for the apparatus. All the features and different variations discussed above with regard to FIGS. 1 and 2 may also be implemented with the embodiment of FIG. 4 and are only not repeated here for the sake of brevity. In some embodiments, the compartment 210 may be completely separatable from the knee brace 140 such that the compartment 210 may be attached to a normal knee brace that the user wears.

Figure 5:
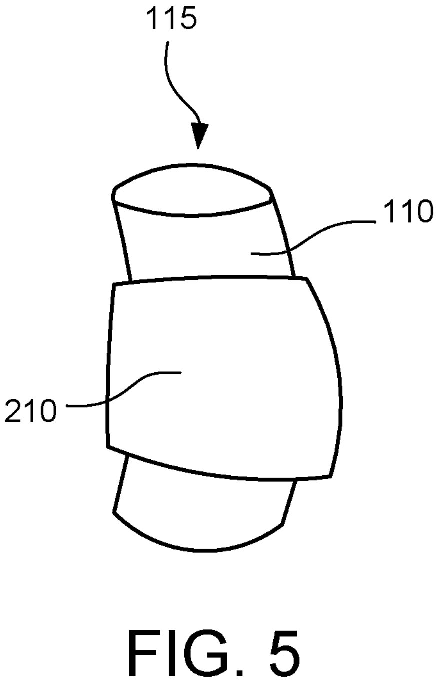
FIG. 5 shows a side view of a knee cushion apparatus according to one or more embodiments of the present disclosure.

FIG. 5 shows a side view of a knee cushion apparatus according to one or more embodiments of the present disclosure. As can be seen by the relative shape of the sleeve 110, this figure is showing what the apparatus would look like on a user's left knee (and being viewed from the inside of the knee. As can be seen, the sleeve 110 extends both above and below the compartment 210 such that the compartment 210 will always be between the top of the sleeve 110 where the upper opening 115 of the sleeve 110 is located and the bottom of the sleeve 110 where the lower opening 122 of the sleeve 110 is located.

As also can be seen in the illustrated embodiment, the compartment 210 may be larger than the sleeve 110 on the sides of the compartment 210. In other words, the compartment 210 (and thus the cushion pads 310) will extend farther than the knee cap and the knee pit of the user. This can just assure that the cushion pads 310 are always covering the inside of the knee such that the knees of the user do not ever contact. This may increase the comfort of the user.

Figure 6:
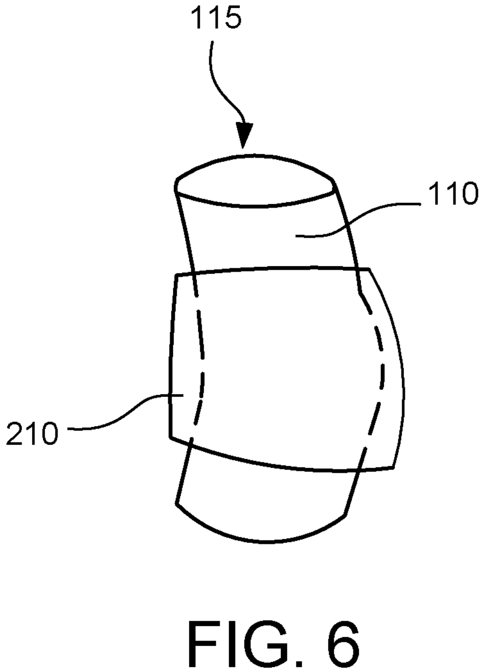
FIG. 6 shows a side view of a knee cushion apparatus according to one or more embodiments of the present disclosure.

FIG. 6 shows a side view of a knee cushion apparatus according to one or more embodiments of the present disclosure. FIG. 6 shows the knee sleeve 110 (with dashed lines) behind the compartment 210 to more easily see how the compartment 210 can extend farther than the knee cap and the knee pit of the user. As shown, the relative size of the compartment 210 may be shown. In other embodiments, the compartment 210 is larger. In some embodiments, the compartment may be smaller. The illustrated embodiment includes a good size extending just an inch above the knee so that the cushion pad is not encroaching to high in between the thighs of the user. A cushion too high may result in an incorrect alignment of the hips, knees, and back. This may be where the quadricep muscle begins or slightly above where the quadricep muscle begins. The illustrated embodiment depicts an irregularly shaped compartment 210. In some embodiments, the compartment 210 is merely a generally rectangular shape (that obviously can adjust because of the flexibility and stretchability of some embodiments).

Figure 7:
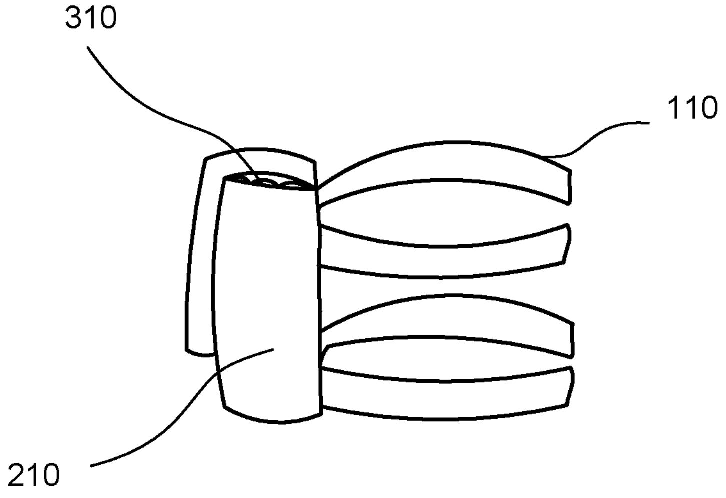
FIG. 7 shows a front view of a knee cushion apparatus according to one or more embodiments of the present disclosure.

FIG. 7 depicts another embodiment of a knee cushion apparatus according to one or more embodiments of the present disclosure. Instead of an all encompassing sleeve, the apparatus includes four straps. Two upper straps that would be fastened above the knee and two lower straps that would be fastened below the knee. These straps may be fastened by Velcro or buttons or the like as they wrap around the leg and secure the apparatus in place on a user's leg. All the features and different variations discussed above with regard to FIGS. 1-6 that would be compatible with straps may also be implemented with the embodiment of FIG. 7 and are only not repeated here for the sake of brevity.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An apparatus comprising:

a sleeve configured to be worn on a leg of a user, wherein the sleeve comprises an upper opening and lower opening, and a compartment coupled to the sleeve, wherein the compartment is configured to be located on an inside of a knee of the user when the sleeve is worn such that the compartment is positioned between the knees of the user, and wherein the upper opening is positioned above the knee of the user and the lower opening is positioned below the knee of the user, and wherein the compartment comprises a compartment opening making an interior of the compartment accessible, and wherein the compartment comprises a flap that is configured to cover the compartment opening;

a compressible padding enclosed within the compartment such that the compressible padding is configured to positioned between a user's knees when they sleep on their side, wherein the sleeve is a tube of material configured to compress on the knee of the user such that the compartment will stay in position relative to the knee and the compressible padding will stay between the knees of the user;

wherein the compressible padding separates the legs of the user to align the legs and back of the user when they sleep on their side, and wherein the padding comprises a plurality of cushion pads, wherein the number of cushion pads can be adjusted by the user to change an overall thickness of the padding between the knees, and wherein when the apparatus is worn on the leg of the user, the compressible padding extends farther to a front than the knee of the user and the compressible padding extends farther to a rear than the knee pit of the user; and wherein the compartment is configured to be below the upper opening of the sleeve and above the lower opening of the sleeve while extending farther to a front than the knee of the user and farther to a rear than the knee pit of the user and wherein the compartment opening is on a side of the compartment adjacent to the upper opening with the flap covering an entirety of the compartment opening when the flap is closed.

2. The apparatus of claim 1, wherein the sleeve is symmetrical from front to back such that either knee of the user may be inserted into the sleeve with the compartment on the inside of the knee.

3. The apparatus of claim 1, wherein the sleeve comprises a hole, wherein the kneecap is configured to sit in the hole.

4. The apparatus of claim 1, wherein the sleeve is made of a flexible and a stretchable fabric.

5. The apparatus of claim 1, wherein the sleeve is configured to be worn on either knee.

6. The apparatus of claim 1, wherein the compartment opening enables the padding is inserted into or removed from the compartment.

7. The apparatus of claim 1, wherein the compartment opening enables the padding to be inserted into or removed from the compartment, wherein the plurality of cushion pads each have differing thicknesses.

8. The apparatus of claim 1, wherein the upper opening and the lower opening are the same size.

9. The apparatus of claim 1, wherein the upper opening is larger in size than the lower opening.

10. An apparatus comprising:

a sleeve configured to be worn on a knee of a user, wherein the sleeve comprises an upper opening and lower opening, and wherein the compartment is configured to be located on an inside of the knee when the sleeve is worn such that a compartment is positioned between the knees of the user, and wherein the upper opening is positioned above the knee of the user and the lower opening is positioned below the knee of the user, and wherein the compartment comprises a compartment opening making an interior of the compartment accessible, and wherein the compartment comprises a flap that is configured to cover the compartment opening, and wherein the compartment is coupled to the sleeve by a stitching, and wherein the stitching runs circumferentially around a back side of the compartment;

a compressible padding enclosed within the compartment such that the compressible padding is configured to positioned between a user's knees when they sleep on their side, wherein the sleeve is a tube of material configured to compress on the knee of the user such that the compartment will stay in position relative to the knee and the compressible padding will stay between the knees of the user; the compartment coupled to the sleeve, wherein the compressible padding separates the legs of the user to align the legs and back of the user when they sleep on their side, and wherein the padding comprises a plurality of cushion pads, wherein the number of cushion pads can be adjusted by the user to change an overall thickness of the padding between the knees, and wherein when the apparatus is worn on the leg of the user, the compressible padding extends farther to a front than the knee of the user and the compressible padding extends farther to a rear than the knee pit of the user; and wherein the compartment is configured to be below the upper opening of the sleeve and above the lower opening of the sleeve while extending farther to a front than the knee of the user and farther to a rear than the knee pit of the user and wherein the compartment opening is on a side of the compartment adjacent to the upper opening with the flap covering an entirety of the compartment opening when the flap is closed.

11. The apparatus of claim 10, wherein the sleeve is symmetrical from front to back such that either knee of the user may be inserted into the sleeve with the compartment on the inside of the knee.

12. The apparatus of claim 10, wherein the sleeve comprises a hole, wherein the kneecap is configured to sit in the hole.

13. The apparatus of claim 10, wherein the sleeve is made of a flexible and a stretchable fabric.

* * * * *